United States Patent [19]

Futami et al.

[11] Patent Number: 5,116,222
[45] Date of Patent: May 26, 1992

[54] LOW-DUSTING POWDERY ALGINATE IMPRESSION MATERIALS FOR DENTAL PURPOSES

[75] Inventors: Shunichi Futami, Nagareyama; Kimihiko Sato, Tokyo, both of Japan

[73] Assignee: G-C Dental Industrial Corp., Tokyo, Japan

[21] Appl. No.: 433,222

[22] Filed: Nov. 8, 1989

[30] Foreign Application Priority Data

Nov. 25, 1988 [JP] Japan .............................. 63-296093
Mar. 1, 1989 [JP] Japan .............................. 1-46480
Sep. 22, 1989 [JP] Japan .............................. 1-245011

[51] Int. Cl.⁵ .............................................. A61C 9/00
[52] U.S. Cl. .................................................... 433/48
[58] Field of Search ......................................... 433/48

[56] References Cited

U.S. PATENT DOCUMENTS 1,672,776  6/1928  Poller ..................................... 433/48

Primary Examiner—V. Millin
Attorney, Agent, or Firm—Oblon, Spivak, McClelland, Maier & Neustadt

[57] ABSTRACT

A low-dusting powdery alginate impression material for dental purposes comprises (a) an alginate, (b) a gelation agent, (c) a gelation controlling agent, (d) a filler, (e) at least one of an oxide, hydroxide and fluoride of a metal and (f) lanolin with or without at least one lanolin derivative, and may further include pigments and perfumes, which provides increased dimensional accuracy, improved manipulatability, improved storage stability, improved dimensional stability and improved surface smoothness.

3 Claims, No Drawings

LOW-DUSTING POWDERY ALGINATE IMPRESSION MATERIALS FOR DENTAL PURPOSES

BACKGROUND OF THE INVENTION

1. Field of the Invention

The present invention relates to a dental alginate impression materials provided in powdery form and, more particularly, to a low-dusting powdery alginate impression material for dental purposes, which is characterized by reducing scattering of dust and excelling in storability and the accuracy of gypsum models.

2. Prior Art

Dental alginate impression materials provided in powdery form have been frequently used over a long term of years, because they are inexpensive and can be employed to prepare an impression in the mouth of suitable accuracy. In use, a predetermined amount of a dental powdery alginate impression material (hereinafter referred to as the alginate impression material) is placed with water in a small rubber bowl, in which they are mixed together with the use of a spatula into a paste. Thereafter, the paste is placed on an impression tray and inserted under pressure into the mouth. After the paste has gelled into an elastomer, it is removed to take an impression in the mouth. Then, gypsum slurry is poured into a negative cast of such an impression to obtain a gypsum model which is usable as a working model for prostheses.

How the surface details of gypsum is reproduced depends upon the fitness of the prepared prosthesis when it is retained in the oral mouth. The surface roughness of the gypsum model is governed by the boundary correlation between the alginate impression material and a gypsum model material. To this end, a material, which promotes or does not interfering with the gelling reaction of the alginate impression material and the solidification of gypsum, should practically be selected and used.

The alginate impression material comprises finely powdered components in order that it is easily formed with water into a paste of which a homogeneous gel elastomer is then formed. In particular, 50 to 80% by weight of finely divided particle powders such as diatomaceous earth, silicic anhydride, talc, calcium carbonate and perlite are generally used for the purpose of reinforcing the gel elastomer.

Powders of such an alginate impression material have a property of settling down during storage and changing gradually in their own bulk density. For that reason, a storage vessel is ordinarily restored to the lowest bulk density by shaking or other means to accurately take a predetermined amount of such powders therefrom with the use of an exclusive spoon having a constant volume.

As the storage vessel is uncovered after shaking, the powders tend to scatter into the air in the form of dust. Dusting also takes place by agitation made with a spatula when a predetermined amount of the powders is mixed with water into a paste in a small bowl of rubber. As heretofore pointed out, a grave problem with the alginate impression material is dusting, since dust does not only give an unpleasant feeling to users but also poses air pollution and health problems.

In order to solve such problems, it has been proposed to coat powder particles of the alginate impression material with a coating agent readily soluble and rapidly wettable in water, as disclosed in Japanese Patent Laid-Open No. 57-501426.

According to the teachings of the specification of the above published patent, the coating agents to be used include natural polymer dispersants such as xanthane rubber and sodium polyalginate; cellulose esters or ethers such as hydroxyethyl cellulose and carboxymethyl cellulose; synthetic nonionic polymer surfactants derived from polyethylene glycol and polypropylene glycol; polyols; alkanolamines; and glycerol esters. Use is also made of a substance having in its molecule a hydrophilic group such as —COOH, —OH, —NH$_2$ or —CH$_2$—CH$_2$O—, which shows good wettability with respect to water or a substitute therefor.

However, problems with the method disclosed in Japanese patent Laid-Open No. 57-501426 are that the water absorptivity of the alginate impression material is so increased that its depolymerization due to the presence of water or the reaction of the alkaline component with the acidic component is promoted, resulting in noticeable deterioration of quality and remarkable reductions in storage and service life.

Nowhere in this specification is referred to the surface accuracy of a gypsum model. The coating agents disclosed therein have a demerit of interfering with or delaying the solidification of gypsum, so that the surface of a gypsum model obtained by pouring gypsum slurry into an impression's negative cast is roughened with a decrease in its accuracy.

Referring next to the technique disclosed in Japanese Patent Laid-Open No. 59-225104, it has for its object to provide a nonionic surface active agent and a hydrophobic liquid having a vapor pressure of 3.15 mmHg or below at 20° C.

This technique is characterized in that scattering of dust is reduced with improvements in storage stability by said hydrophobic liquid component comprising combinations of hydrocarbons, fatty acids, alcohols, oils, silicone and so on, but fails to smooth the surface of a gypsum model and thereby improve the accuracy thereof.

The nonionic surfactant does not interfere with the gelling reaction of the alginate impression material of the solidification of gypsum, but is found to be ineffective for smoothing the surface of a gypsum model.

The technique disclosed in Japanese Patent Laid-Open No. 60-105607 issued under the name of the same inventors as in Japanese Patent Laid-Open No. 59-225104 is characterized in that scattering of dust is reduced with improvements in storage stability, the surface smoothness of gypsum models and impression accuracy by using a composition comprising a combination of at least one of a liquid hydrocarbon showing hydrophobic properties and having a vapor pressure of 3.15 mmHg or less at 20° C. and a silicone oil with polyvinyl pyrrolidone, but does not aim at improving dimensional stability and accuracy.

Polyvinyl pyrrolidone is effective for smoothing the surface of gypsum models and impression accuracy, and the hydrophobic hydrocarbon and silicone oil excel in terms of storage stability and the prevention of scattering of powders. However, they are all so lacking in water retention that dimensional stability of the alginate impression material is reduced.

Main object of the present invention is, therefore, to provide an alginate impression material which reduced dusting, excels in storage stability, imparts improved surface smoothness and accuracy to gypsum models obtained by pouring gypsum slurry into negative casts of impressions, and can give gypsum models of accuracy increased by improvements in dimensional stability. As a result of intensive and extensive studies made to this end, the present inventors have found that the above object is achievable by incorporating lanolin with or without at least one lanolin derivative into alginate impression material compositions.

According to the present invention accomplished with the water entraining properties of lanolin in mind, it is possible to reduce scattering of powdery alginate impression materials, improve their storage stability, smooth the surface of gypsum models with increased impression accuracy and improve dimensional accuracy due to improvement sin dimensional stability.

SUMMARY OF THE INVENTION

Thus, the present invention provides an alginate impression material comprising (a) an alginate, (b) a gelation agent, (c) a gelation controlling agent, (d) a filler, (e) at least one of an oxide, hydroxide and fluoride of a metal and (f) lanolin with or without at least one lanolin derivative as well as other known additives to be added, if required.

DETAILED DESCRIPTION OF THE INVENTION

In the prior art, it has been proposed to use coating agents wettable by water in methods for coating alginate powder particles with a view to making low-dusting powdery alginate impression materials. However, they are as a whole so high in water absorptivity that they show increased tendency toward absorbing atmospheric moisture, giving rise to deteriorations of their quality. In order to provide a solution to this, it has also been proposed to rely upon a hydrophobic liquid and a nonionic surfactant or polyvinyl pyrrolidone. Although they have an effect upon low-dusting properties, storage stability and the surface smoothness of gypsum models, yet they are found to fail to improve dimensional stability. With the present invention, however, it is achievable for the first time to provide an alginate impression material of increased dimensional accuracy, which is improved in terms of manipulatability, low-dusting properties, storage stability and dimensional stability as well as the surface smoothness of gypsum models by using as the component (f) lanolin with or without at least one lanolin derivative.

As the alginate that is the component (a), use may be made of at least one of water-soluble salts of alginic acid such as its sodium, potassium, ammonium and triethanolamine salts.

As the gelation agent that is the component (b), a slightly soluble salt of a di- or more-valent metal may be used. However, preference is given to calcium sulfate dihydrate and/or hemihydrate.

As the gelation controlling agent that is the component (c), use may be made of at least one of various phosphates, silicates or carbonates of sodium or potassium.

As the filler that is the component (d), use may made of at least one of finely divided powders such as those of diatomaceous earth, silicic anhydride, talc, calcium carbonate and perlite.

As the oxide, hydroxide and fluoride of a metal that is the component (e), use may be made of at least one of zinc oxide, aluminium oxide, magnesium oxide, magnesium hydroxide, lead hydroxide, an oxide or hydroxide of other di- or more-valent metal, potassium silicofluoride, sodium silicofluoride, potassium titanium fluoride, potassium fluoride, sodium fluoride and a fluoride of other metal.

If required, use may be additionally made of pigments and perfumes.

In the present invention, any particular limitation is not imposed on the components (a), (b), (c), (d) and (e). To put it another way, the present invention provides a dental impression material in which an alginate is used as gelling component-forming source and which is available in powdery form, and is characterized by containing therein lanolin with or without at least one lanolin derivative as the component (f).

Lanolin that is the component (f) is obtained by refining a waxy substance adhering to wool and referred to as wool grease or wax. Chemically, lanolin is an ester of a higher alcohol with a fatty acid, i.e., a wax, whereas tallow and lard are glycerides. A part of the fatty acid contains a hydroxide group. Lanolin including such a unique wax comprises hydroxyester, hydroxyfatty acids and free alcohols and is found to be less irritative and more spreadable and, in particular, possesses water entraining properties. To add to this, lanolin is neither hydrophilic nor water-soluble, but is nonetheless found to be sufficiently mixable and dispersible with water. With the present invention accomplished in view of the foregoing considerations, improvements in dimensional stability in both atmospheric and aqueous environments, hitherto unprecedented, are achievable by using lanolin.

Use of lanolin in combination with the lanolin derivative soluble in water makes mixing with water easier than its sole use. This aspect of the present invention is additionally characterized in that an impression is so smoothed on its surface that a precise gypsum model can be obtained with no dent on its surface and, hence, no air bubbles or convexities thereon. The lanolin derivaties used in the present invention may include acetyl lanolin, olanolin alcohols and reduced lanolin and so on.

Preferably, the lanolins and their derivatives used to make the low-dusting powdery alginate impression materials which are improved in terms of low-dusting properties, storage stability, mixability after storage and the surface smoothness and dimensional stability of gypsum models are typically a liquid lanolin and a liquid lanolin alcohol (that is a hydrophilic and water-soluble lanolin derivative), which, if liquid at normal temperature, have advantages of being easily mixable with powdery components and easily processable.

In order to obtain the hydrophilic and water-soluble lanolin derivative, lanolin is usually ethoxylated, but it is obtained by the addition polymerization of ethylene oxide. Consequently, the product is increased in water solubility but assumes a waxy solid at normal temperature. For that reason, polyoxyethylene (PEG) or polyoxypropylene (PPG) lanolin that is a hydrophilic or water-soluble liquid at normal temperature is obtained by the addition polymerization of propylene oxide for use. Depending upon the quantity and ratio of PEG and PPG, a hydrophilic or water-soluble liquid lanolin derivative is also prepared for use. In order to obtain low-dusting powdery alginate impression materials which are improved in terms of low-dusting properties, storage stability, mixability after storage and the surface smoothness and dimensional accuracy of gypsum models, the lanolin with or without at least one lanolin derivative should preferably be used in a quantity of 1.0 to 20.0% by weight. At less than 1.0% by weight, it is less effective for reducing scattering of powders, while at more than 20.0% by weight, there is a decrease in the strength of the gel. It is to be understood that when the lanolin is used in combination with at least one lanolin derivative, it is preferable to use the lanolin in a quantity of 1.0% by weight of more.

The present invention is characterized by the provision of a dental alginate impression material containing an alginate as a gel-forming source. The alginate impression materials according to the present invention can be manipulated by users with no fear of air pollution or health problem, since no dusting takes place at all when their storage vessel is shaken or they are mixed for use.

Furthermore, their quality can be maintained over an extended period of time; and they make it possible to improve the surface accuracy of gypsum moldes obtainable from negative casts of impressions and obtain gypsum models of high dimensional accuracy which are improved in terms of dimensional stability in both atmospheric and aqueous environments.

EXAMPLES

In what follows, the present invention will now be explained specifically but not exclusively with reference to the following examples.

EXAMPLE 1

| Ingredients | Parts by Weight |
|---|---|
| Sodium alginate | 14 |
| Calcium sulfate dihydrate | 15 |
| Sodium pyrophosphate | 2 |
| Diatomaceous earth | 48 |
| Talc | 6 |
| Potassium titanium fluoride | 2 |
| Aluminium oxide | 2 |

The above ingredients were mixed together in a blender. While mixing was further continued in the blender, 11 parts by weight of lanolin (available from Takasago Koryo Kogyo Co., Ltd under the trade name of Refined Lanolin FP) warmed to 45° C. were added dropwise. Sixteen (16) parts by weight of the obtained powders and 40 parts by weight of water were placed in a rubber bowl and mixed together with the use of a spatula. Six (6) seconds after the initiation of mixing, wetting of water into the powders was observed, and after the lapse of 30 seconds, a homogeneous paste was obtained. The gelled product was measured on its linear shrinkage after allowed to stand at a room temperature of 23° C. and a humidity of 50% for 1 hour. As a result, it showed a shrinkage of 1.6%, the figure being as low as 50 to 60% of a conventional product. A dimensional change (expansion) in water was 0.3%, the figure being as little as about ⅓ of that in the comparative example.

EXAMPLE 2

In this example, 4 parts by weight of lanolin (manufactured by Yoshikawa Seiyu Co., Ltd and available under the trade name of YOFCO Lanolin)) were used in place of 11 parts by weight of lanolin (manufactured by Takasago Koryo Kogyo Co., Ltd and available under the trade name of Refined Lanolin FP), and the amount of diaomaceous earth was increased to 7 parts by weight. According to otherwise similar procedures as stated in Example 1, the above powdery ingredients were mixed together in a blender and 4 parts by weight of sad lanolin warmed to 50° C. were added dropwise therein.

Sixteen (16) parts by weight of the obtained powders and 40 parts by weight of water were placed in a rubber bowl and mixed together with the use of a spatula. After five seconds of the initiation of mixing, wetting of water into the powders were observed, and after the passage of 20 seconds, a homogeneous paste was obtained. During mixing, dusting was not found. The gelled product was measured on its linear shrinkage after allowed to stand at a room temperature of 23° C. and a humidity of 50% for 1 hour. As a result, it showed a shrinkage of 1.7%, the figure being as low as 40 to 50% of a conventional product. A dimensional change (expansion) in water was 0.4%, the figure being as little as about ½ to ⅓ of that in the comparative example.

EXAMPLE 3

| Ingredients | Parts by Weight |
|---|---|
| Potassium alginate | 14 |
| Calcium sulfate dihydrate | 15 |
| Trisodium phosphate | 2 |
| Finely divided silicic anhydride | 6 |
| Diatomaceous earth | 46 |
| Perlite | 4 |
| Potassium silicofluoride | 2 |
| Zinc oxide | 3 |

The above ingredients were placed and mixed together in a blender. While mixing was further continued, 8 parts by weight of lanolin (manufactured by Croda Japan Co., Ltd. and available under the trade name of Refined Lanolin) were warmed to 50° C., followed by dropwise addition.

Sixteen (16) parts by weight of the obtained powders and 40 parts by weight of water were placed in a rubber bowl and mixed together with the use of a spatula. After five seconds of the initiation of mixing, wetting of water into the powders was observed, and after the passage of 25 seconds, a homogeneous paste was obtained. During mixing, dusting was not found. The gelled product was measured on its linear shrinkage after allowed to stand at a room temperature of 23° C. and a humidity of 50% for 1 hour. As a result, it was found to show a shrinkage of 1.4%, the figure being as low as 50% of a conventional product. A dimensional change (expansion) in water was 0.3%, the figure being as little as about ⅓ of the comparative example.

EXAMPLE 4

| Ingredients | Parts by Weight |
|---|---|
| Sodium alginate | 14 |
| Calcium sulfate dihydrate | 15 |
| Sodium pyrophosphate | 2 |
| Diatomaceous earth | 50 |
| Talc | 5 |
| Potassium titanium fluoride | 1 |
| Aluminium oxide | 2 |

The above ingredients were mixed together in a blender. While mixing was further continued in the blender, 3 parts by weight of lanolin (available from Takasago Koryo Kogyo Co., Ltd under the trade name of Refined Lanolin FP) and 8 parts by weight of ethylene-modified lanolin (containing 50 moles of ethylene oxide and 12 moles of propylene oxide by addition polymerization, manufactured by Croda Japan Co., Ltd. and available under the trade name of Lanexol AWS) were warmed to 40° C. and mixed together, followed by dropwise addition.

Sixteen (16) parts by weight of the obtained powders and 40 parts by weight of water were placed in a rubber bowl and mixed together with the use of a spatula. After five seconds of the initiation of mixing, wetting of water into the powders was observed, and after the lapse of 30 seconds, a homogeneous paste was obtained. The gelled product was measured on its linear shrinkage after allowed to stand at a room temperature of 23° C. and a humidity of 50% for 1 hour. As a result, it showed a shrinkage of 1.5%, the figure being as low as 50 to 60% of a conventional product. A dimensional change (expansion) in water was 0.5%, the figure being as little as about ½ of the comparative example.

EXAMPLE 5

In this example, 3 parts by weight of liquid lanolin (manufactured by Takasago Koryo Kogyo Co., Ltd and available under the trade name of Reolane) were used in place of 3 parts by weight of the lanolin used in Example 4; 2.5 parts by weight of ethylenemodified reduced lanolin (containing 20 moles of ethylene oxide and 20 moles of propylene oxide by addition polymerization, manufactured by Croda Japan Co., Ltd. and available under the trade name of Prochol WH-4000) were employed in lieu of 8 parts by weight of the ethylene-modified lanolin used in Example 4; and the amount of diamoaceous earth was increased to 5.5 parts by weight. According to otherwise similar procedures as stated in Example 4, the above powdery ingredients were mixed together in a blender and 3 parts by weight of said liquid lanolin and 2.5 parts by weight of said ethylene-modified reduced lanolin were added dropwise therein.

Sixteen (16) parts by weight of the obtained powders and 40 parts by weight of water were placed in a rubber bowl and mixed together with the use of a spatula. After five seconds of the initiation of mixing, wetting of water into the powders was observed, and after the passage of 20 seconds, a homogeneous paste was obtained. During mixing, dusting was not found. The gelled product was measured on its linear shrinkage after allowed to stand at a room temperature of 23° C. and a humidity of 50% for 1 hour. As a result, it showed a shrinkage of 1.7%, the figure being as low as 40 to 50% of a conventional product. A dimensional change (expansion) in water was 0.6%, the figure being as little as about 3/5 of the comparative example.

EXAMPLE 6

| Ingredients | Parts by Weight |
| --- | --- |
| Potassium alginate | 14 |
| Calcium sulfate dihydrate | 15 |
| Trisodium phosphate | 2 |
| Finely divided silicic anhydride | 8 |
| Diatomaceous earth | 35 |
| Perlite | 6 |
| Potassium silicofluoride | 1 |
| Zinc oxide | 3 |

The above ingredients were placed and mixed together in a blender. While mixing was further continued, 3 parts by weight of liquid lanolin (manufactured by Takasago Koryo Kogyo Co., Ltd. and available under the trade name of Reolan), 1 part by weight of acetyl lanolin (manufactured by Takasago Koryo Kogyo Co., Ltd. and available under the trade name of Lanocetyl-L) and 12 parts by weight of lanolin alcohol (containing 15 moles of ethylene oxide by addition polymerization, manufactured by Takasago Koryo Kogyo Co., Ltd. and available under the trade name of Lanopol A-170) were warmed to 40° C., followed by dropwise addition.

Sixteen (16) parts by weight of the obtained powders and 40 parts by weight of water were placed in a rubber bowl and mixed together with the use of a spatula. After five seconds of the initiation of mixing, wetting of water into the powders was observed, and after the passage of 25 seconds, a homogeneous paste was obtained. During mixing, dusting was not found. The gelled product was measured on its linear shrinkage after allowed to stand at a room temperature of 23° C. and a humidity of 50% for 1 hour. As a result, it was found to show a shrinkage of 1.6%, the figure being as low as 50% of a conventional product. A dimensional change (expansion) in water was 0.6%, the figure being as little as about 3/5 of the comparative example.

EXAMPLE 7

| Ingredients | Parts by Weight |
| --- | --- |
| Potassium alginate | 12 |
| Calcium sulfate hemihydrate | 7 |
| Calcium sulfate dihydrate | 7 |
| Sodium tripolyphosphate | 1.5 |
| Diatomaceous earth | 48 |
| Finely divided silicic anhydride | 17 |
| Sodium silicofluoride | 2 |
| Magnesium hydroxide | 2 |

The above ingredients were mixed together in a blender. While mixing was further continued in the blender, 3.5 parts by weight of liquid lanolin (available from Takasago Koryo Kogyo Co., Ltd under the trade name of Reolan) were added dropwise thereto.

Sixteen (16) parts by weight of the obtained powders and 40 parts by weight of water were placed in a rubber bowl and mixed together with the use of a spatula. After five seconds of the initiation of mixing, wetting of water into the powders was observed, and after the lapse of 30 seconds, a homogeneous paste was obtained. The gelled product was measured on its linear shrinkage after allowed to stand at a room temperature of 23° C. and a humidity of 50% for 1 hour. As a result, it showed a shrinkage of 1.3%, the figure being as low as about ½ to ⅓ of a conventional product. A dimensional change (expansion) in water was 0.4%, the figure being as little as about ½ to ⅓ of the comparative example.

COMPARATIVE EXAMPLE 1

The procedures of Example 3 were repeated, provided that the amounts of diatomaceous earth and finely divided silicic anhydride were increased by 6 and 2 parts by weight, respectively, in the absence of the lanolin. Required for wetting of water into the powders were 15 seconds and dusting occurred during mixing. The gelled product showed a linear shrinkage of 3.2% as a result of measurement at a room temperature of 23° C. and a humidity of 50% for 1 hour. A dimensional change (expansion) in water was 1.3%.

COMPARATIVE EXAMPLE 2

The procedures of Example 3 were repeated, provided that 3 parts by weight of such polyoxyethylene (20) sorbitan monolaurate as described in Japanese Patent Laid-Open No. 57-501426 were added and the amount of diatomaceous earth was increased by 5 parts by weight in the absence of the lanolin. Required for wetting of water into the powders were 5 seconds and no dusting occurred during mixing. However, the gelled product showed a linear shrinkage of 3.1% as a result of measurement at a room temperature of 23° C. and a humidity of 50% for 1 hour. A dimensional change (expansion) in water was 1.0%.

COMPARATIVE EXAMPLE 3

The procedures of Example 3 were repeated, provided that 1 part by weight of such polyvinyl pyrrolidone as described in Japanese Patent Laid-Open No. 60-105607 (having a molecular weight of 2500, manufactured by BASF and available under the trade name of Colidone 12PF) and 3 parts by weight of liquid paraffin were added and the amount of diatomaceous earth was increased by 4 parts by weight in the absence of the lanolin. Required for wetting of water into the powders were 5 seconds and no dusting occurred during mixing. However, the gelled product showed a linear shrinkage of 2.9% as a result of measurement at a room temperature of 23° C. and a humidity of 50% for 1 hour. A dimensional change (expansion) in water was 0.8%.

The alginate impression materials obtained according to the examples and comparison examples were measured on their setting time, compressive strength and setting time and compressive strength before and after forced degradation according to American Dental Association Specification No. 18. The results are tabulated below with the concentration by weight of dust released and dimensional changes of impression in the atmosphere and water and the surface roughness of gypsum obtained from impressions, all measured as will be described later.

Dimensional Change in the Atmosphere

This was measured according to American Dental Association Specification No. 19. After 10 minutes of the initiation of mixing at a room temperature of 23° C. and a humidity of 50%, two reference lines were marked on a sample piece removed from a mixing die in sheet form. With an 1/1,000 mm accurate measuring unit (a comparator made by Shimazu Seisakusho Co., ltd.), the distance between both reference lines was first measured to obtain a measurement A, and again determined to obtain B after the lapse of 1 hour. The dimensional change was thus calculated by the following equation:

$$\text{Dimensional Change (Linear Shrinkage)} = \frac{A - B}{A} \times 100$$

Dimensional Change in Water

This was measured according to American Dental Association Specification No. 19. After 10 minutes of the initiation of mixing at a room temperature of 23° C. and a humidity of 50%, two reference lines were marked on a sample piece removed from a mixing die in sheet form. With an 1/1,000 mm accurate measuring unit (a comparator made by Shimazu Seisakusho Co., Ltd.), the distance between both reference lines was first measured as such to obtain a measurement $A'$, and again determined in water of 23° C. to obtain $B'$ after the lapse of 1 hour. The dimensional change was thus calculated by the following equation:

$$\text{Dimensional Change (Linear Expansion)} = \frac{B' - A'}{A'} \times 100.$$

Surface Roughness of Gypsum

Measured (1) according to JIS B 0601 (2) with a measuring unit (available under the trade name of Surfcoder SE-40H from Kosaka Kenkyusho Co., Ltd.).

TABLE

| Samples | | Concentration by weight of dust (mg/m³) | Setting time | Setting time after forced degradation | Compressive strength (kg/cm²) | Compressive strength after forced degradation (kg/cm²) | Dimensional changes in atmosphere (after one hour) (%) | Dimensional changes in water (after one hour) (%) | Surface roughness of gypsum (μm) |
|---|---|---|---|---|---|---|---|---|---|
| Examples | 1 | 1.2 | 2' 30" | 2' 30" | 10.0 | 8.5 | 1.6 | 0.3 | 7.0 |
| | 2 | 1.3 | 2' 30" | 2' 20" | 8.0 | 7.0 | 1.7 | 0.4 | 6.5 |
| | 3 | 1.2 | 2' 30" | 2' 30" | 9.5 | 8.0 | 1.4 | 0.3 | 6.0 |
| | 4 | 1.4 | 2' 20" | 2' 30" | 8.0 | 6.5 | 1.5 | 0.5 | 6.0 |
| | 5 | 1.5 | 2' 30" | 2' 20" | 7.5 | 6.5 | 1.7 | 0.6 | 7.0 |
| | 6 | 1.2 | 2' 20" | 2' 20" | 8.5 | 7.0 | 1.6 | 0.6 | 6.5 |
| | 7 | 1.3 | 2' 10" | 2' 20" | 7.4 | 7.0 | 1.3 | 0.4 | 7.0 |
| Comparative Examples | 1 | 28.4 | 2' 30" | 4' 00" | 8.0 | 3.5 | 3.2 | 1.3 | 12.5 |
| | 2 | 2.6 | 2' 20" | 1' 00" | 7.5 | 1.8 | 3.1 | 1.0 | 16.0 |
| | 3 | 1.5 | 2' 20" | 2' 30" | 9.0 | 7.5 | 2.9 | 0.8 | 7.2 |

Concentration by Weight of Dust

One hundred and fifty (150) g of a sample were placed in a round metal can (of $\phi$ 150×135 mm), which was then vertically shaken five times per second. Just thereafter, the can was uncovered to measure the concentration by weight of dust released therefrom with a digital dust meter, Type P-3 (made by Shibata Kagaku Co., Ltd.) for one minute.

After taking an impression of a mirror surface, gypsum cast therein was solidified at 100% humidity and removed after 1 hour. After the passage of one day, measurement was carried out.

From the results set out in the table, it is found that the set product of the alginate impression material of Comparative Example 1 after forced degradation fluctuates largely in its properties, as expressed in terms of compressive strength dropping to ½ or below, increased dusting and high dimensional change.

The impression material of Comparative Example 2 after forced degradation fluctuates largely in setting time, shows a compressive strength dropping to as little as ¼ or less and imparts increased roughness to the surface of gypsum.

The dimensional accuracy of the negative cast of an impression according to the present invention is much improved over that due to a relatively large dimensional change of the negative cast of an impression obtained with the alginate impression materials of Comparative Examples 1 to 3. It is thus noted that a model of more improved dimensional accuracy and performance can be obtained by pouring gypsum slurry into a negative cast of an impression with the present impression materials.

As mentioned above, the present invention can provide an alginate impression material which is improved in terms of not only low-dusting properties, storage stability and the surface smoothness of gypsum models but also dimensional stability and hence dimensional accuracy.

What is claimed is:

1. A low-dusting powdery alginate impression material for dental purposes, comprising:
   (a) an alginate,
   (b) a gelation agent,
   (c) a gelation controlling agent,
   (d) a filler,
   (e) at least one of an oxide, hydroxide and fluoride of a metal, and
   (f) lanolin.

2. A low-dusting powdery alginate impression material for dental purposes, comprising:
   (a) an alginate,
   (b) a gelation agent,
   (c) a gelation controlling agent,
   (d) a filler,
   (e) at least one of an oxide, hydroxide and fluoride of a metal, and
   (f) lanolin and at least one lanolin derivative.

3. An alginate impression material as claimed in claim 1 or 2, which further contains pigments and perfumes.

* * * * *